United States Patent
Fukuzawa et al.

(10) Patent No.: US 7,304,734 B2
(45) Date of Patent: Dec. 4, 2007

(54) FLUORESCENCE ANALYSIS OPTICAL MULTIPLEXER/DEMULTIPLEXER, FLUORESCENCE ANALYSIS OPTICAL MODULE, FLUORESCENCE ANALYZER, FLUORESCENCE/PHOTOTHERMAL CONVERSION SPECTROSCOPIC ANALYZER, AND FLUORESCENCE ANALYSIS CHIP

(75) Inventors: Takashi Fukuzawa, Sagamihara (JP); Jun Yamaguchi, Sagamihara (JP); Akihiko Hattori, Sagamihara (JP); Takao Miwa, Sagamihara (JP)

(73) Assignee: Nippon Sheet Glass Company Limited, Tokyo (JP)

( * ) Notice: Subject to any disclaimer, the term of this patent is extended or adjusted under 35 U.S.C. 154(b) by 151 days.

(21) Appl. No.: 11/329,456

(22) Filed: Jan. 9, 2006

(65) Prior Publication Data

US 2006/0109465 A1 May 25, 2006

Related U.S. Application Data

(63) Continuation of application No. PCT/JP2004/009582, filed on Jun. 30, 2004.

(30) Foreign Application Priority Data

Jul. 9, 2003 (JP) ............................. 2003-194408

(51) Int. Cl.
*G01J 3/30* (2006.01)
(52) U.S. Cl. .......................... 356/317; 385/15; 385/31; 385/33; 385/49
(58) Field of Classification Search ................ 356/317, 356/417, 432, 442; 385/15, 31, 49
See application file for complete search history.

(56) References Cited

FOREIGN PATENT DOCUMENTS

JP 5-157628 A 6/1993

JP 11-118716 A 4/1999

(Continued)

*Primary Examiner*—Gregory J. Toatley, Jr.
*Assistant Examiner*—Abdullahi Nur
(74) *Attorney, Agent, or Firm*—Cohen Pontani Lieberman & Pavane LLP

(57) ABSTRACT

A fluorescence analysis optical multiplexer/demultiplexer, a fluorescence analysis optical module, a fluorescence analyzer, a fluorescence/photothermal conversion spectroscopic analyzer, and a fluorescence analysis chip, according to which LIF analysis can be carried out easily and with high sensitivity, and moreover photothermal conversion spectroscopic analysis can be carried out easily and simultaneously with the LIF analysis. A microchemical system 100 as the fluorescence analyzer is comprised of a fluorescence analysis optical module 100a, a probe 50 that condenses exciting light onto a sample solution in a channel 204 inside a fluorescence analysis chip 20, and a sample stage 21 on which the fluorescence analysis chip 20 is mounted. The fluorescence analysis optical module 100a is comprised of an exciting light source 53 that outputs exciting light of dominant wavelength $\lambda_1$, a fluorescence analysis optical multiplexer/demultiplexer 56 for use in the fluorescence analyzer which analyzes fluorescence of dominant wavelength $\lambda_2$ ($\lambda_2 > \lambda_1$) emitted from the sample upon the sample being irradiated with the exciting light via the probe 50, a detector 54 that receives the fluorescence, an optical fiber 106 that connects the fluorescence analysis optical multiplexer/demultiplexer 56 to the exciting light source 53, an optical fiber 107 that connects the fluorescence analysis optical multiplexer/demultiplexer 56 to the probe 50, and an optical fiber 108 that connects the fluorescence analysis optical multiplexer/demultiplexer 56 to the detector 54. The channel 204 through which the sample solution is passed is coated with a reflective metal film 205.

29 Claims, 8 Drawing Sheets

FOREIGN PATENT DOCUMENTS

| | | | | | | |
|---|---|---|---|---|---|---|
| JP | 2002-207009 A | 7/2002 | | JP | 2002-277396 A | 9/2002 |
| JP | 2002-243641 A | 8/2002 | | JP | 2002-296234 A | 10/2002 |
| | | | | WO | WO 01/14849 A1 | 3/2001 |

US 7,304,734 B2

FLUORESCENCE ANALYSIS OPTICAL MULTIPLEXER/DEMULTIPLEXER, FLUORESCENCE ANALYSIS OPTICAL MODULE, FLUORESCENCE ANALYZER, FLUORESCENCE/PHOTOTHERMAL CONVERSION SPECTROSCOPIC ANALYZER, AND FLUORESCENCE ANALYSIS CHIP

This application is a U.S. Continuation Application of International Application PCT/JP2004/009582 filed 30 Jun. 2004.

TECHNICAL FIELD

The present invention relates to a fluorescence analysis optical multiplexer/demultiplexer, a fluorescence analysis optical module, a fluorescence analyzer, a fluorescence/photothermal conversion spectroscopic analyzer, and a fluorescence analysis chip, and more particularly to a fluorescence analysis optical multiplexer/demultiplexer, a fluorescence analysis optical module, a fluorescence analyzer, a fluorescence/photothermal conversion spectroscopic analyzer, and a fluorescence analysis chip which carry out laser induced fluorescence analysis and photothermal conversion spectroscopic analysis.

BACKGROUND ART

Microchemical systems are systems for carrying out highly sensitive detection or analysis on a very small amount of a sample using a capillary tube or a fluorescence analysis chip. For example, a fluorescence analysis chip has provided therein a very fine channel through which a solution containing a very small amount of a sample (a sample solution) flows. The channel may have any of various forms, for example a branching channel or a merging channel, or a meandering channel.

As methods for highly sensitive detection as described above, photothermal conversion spectroscopic analysis and laser induced fluorescence (LIF) analysis have been known from hitherto. LIF analysis is a method in which targeted fluorescent molecules are subjected to electron excitation by a laser, and fluorescence emitted when the excited electrons drop back down to the ground state is measured. A resonant transition between energy levels is used, and hence the probability of excitation is high, and thus detection is possible with very high sensitivity.

For example, as prior art, there has been disclosed a system in which exciting light is convergently irradiated onto a sample flowing through a very fine channel formed in a small glass substrate or the like via a lens from a bottom surface of the channel, and fluorescence thus emitted by the sample is detected from a side of the channel (see, for example, Japanese Laid-open Patent Publication (Kokai) No. 2002-214194).

A problem of such a microchemical system according to the prior art is that the optical systems and so on for light sources, a measurement section and a detection section (photoelectric conversion section) have a complex construction, and hence the system is large in size and lacking in portability, and thus there are limitations with regard to the installation site and the operation of the apparatus, resulting in the work efficiency for users being poor. As prior art solving this problem, there has been disclosed a microchemical system in which exciting light is convergently irradiated onto a sample flowing through a channel formed in a small glass substrate or the like via a lens from an upper surface of the channel, and fluorescence thus emitted by the sample is led to a detector by a lens in the upper surface of the channel, whereby the microchemical system when configured for carrying out LIF analysis can be made compact in size overall (see, for example, Japanese Laid-open Patent Publication (Kokai) No. 2002-131280).

However, in the prior art described above, the exciting light is led to a lens, and the fluorescence is led out via the lens, and hence a dichroic mirror must be disposed in the microchemical system inclined at 45° to the optical axis of the exciting light. Due to differences in wavelength characteristics between P polarized light and S polarized light, the boundary between a reflected wavelength band and a transmitted wavelength band is broadened, and hence of light outputted from the sample, light other than the fluorescence may enter the detector, resulting in it not being possible to carry out LIF analysis accurately.

Moreover, the sample flowing through the channel emits fluorescence isotropically, and hence in the case of carrying out LIF analysis using a system constructed as described above, only the fluorescence emitted toward the detector can be detected. There has thus been a limit on the ability to carry out analysis and identification of substances that emit fluorescence weakly.

Moreover, there have been no microchemical systems capable of carrying out both LIF analysis as described above and photothermal conversion spectroscopic analysis, and hence there has been the problem of it being necessary to provide separate systems for each.

It is an object of the present invention to provide a fluorescence analysis optical multiplexer/demultiplexer, a fluorescence analysis optical module, a fluorescence analyzer, a fluorescence/photothermal conversion spectroscopic analyzer, and a fluorescence analysis chip, according to which LIF analysis can be carried out easily and with high sensitivity, and moreover photothermal conversion spectroscopic analysis can be carried out easily and simultaneously with the LIF analysis.

DISCLOSURE OF THE INVENTION

To attain the above object, according to the present invention, there is provided a fluorescence analysis optical multiplexer/demultiplexer for use in a fluorescence analyzer that analyzes fluorescence of dominant wavelength $\lambda_2$ emitted from a sample onto which has been irradiated exciting light of dominant wavelength $\lambda_1$, wherein $\lambda_2 > \lambda_1$, the fluorescence analysis optical multiplexer/demultiplexer comprising a first lens that receives the exciting light and the fluorescence, a wavelength-selecting material portion comprising a dielectric multilayer film that receives the exciting light and the fluorescence transmitted through the first lens, and a second lens that receives the fluorescence transmitted through the wavelength-selecting material portion.

According to the fluorescence analysis optical multiplexer/demultiplexer of the present invention, the fluorescence analysis optical multiplexer/demultiplexer is for use in a fluorescence analyzer that analyzes fluorescence of dominant wavelength $\lambda_2$ emitted from a sample onto which has been irradiated exciting light of dominant wavelength $\lambda_1$ wherein $\lambda_2 > \lambda_1$, and comprises a first lens that receives the exciting light and the fluorescence, a wavelength-selecting material portion comprising a dielectric multilayer film that receives the exciting light and the fluorescence transmitted through the first lens, and a second lens that receives the fluorescence transmitted through the wavelength-selecting material portion. As a result, the exciting light, which has a relatively high intensity compared with the intensity of the fluorescence emitted from the sample, can be effectively blocked, and hence noise when detecting the fluorescence can be reduced. LIF analysis can thus be carried out easily and with high sensitivity.

Moreover, preferably, the dielectric multilayer film is a long pass filter having a cutoff wavelength between the dominant wavelength $\lambda_1$ and the dominant wavelength $\lambda_2$.

According to the fluorescence analysis optical multiplexer/demultiplexer of the above embodiment, the dielectric multilayer film is a long pass filter having a cutoff wavelength between the dominant wavelength $\lambda_1$ and the dominant wavelength $\lambda_2$. As a result, the transmission loss for the exciting light, which would cause noise in the fluorescence measurement if transmitted through the wavelength-selecting material portion so as to reach a detector for the fluorescence, can be effectively increased, and moreover the exciting light is reflected by the wavelength-selecting material portion, and hence a good amount of exciting light being irradiated onto the sample can be secured.

Moreover, preferably, the transmittance of the wavelength-selecting material portion to light of the dominant wavelength $\lambda_1$ is not more than −30 dB.

According to the fluorescence analysis optical multiplexer/demultiplexer of the above embodiment, the transmittance of the wavelength-selecting material portion to light of the dominant wavelength $\lambda_1$ is not more than −30 dB. As a result, even if the number of layers formed on one another in the dielectric multilayer film is low, the exciting light can be reliably prevented from being transmitted through the fluorescence analysis optical multiplexer/demultiplexer, and hence the measurement/detection noise level for $\lambda_2$ can be effectively reduced.

Moreover, preferably, the transmittance of the wavelength-selecting material portion to light of the dominant wavelength $\lambda_2$ emitted from the sample is not less than −3 dB.

According to the fluorescence analysis optical multiplexer/demultiplexer of the above embodiment, the transmittance of the wavelength-selecting material portion to light of the dominant wavelength $\lambda_2$ emitted from the sample is not less than −3 dB. As a result, good detection signal intensity for the fluorescence transmitted through the fluorescence analysis optical multiplexer/demultiplexer can be secured.

Moreover, preferably, each of the first lens and the second lens is a cylindrical gradient index rod lens provided with a refractive index gradient such that the refractive index decreases from the center of the lens outward.

According to the fluorescence analysis optical multiplexer/demultiplexer of the above embodiment, each of the first lens and the second lens is a cylindrical gradient index rod lens provided with a refractive index gradient such that the refractive index decreases from the center of the lens outward. As a result, each of the end faces, i.e. the input face and the output face, of each of the lenses is a flat face perpendicular to the optical axis, and hence assembly such as joining the lenses together can be carried out easily. Moreover, because each of the lenses is cylindrical, the lenses can easily be housed in a cylindrical holder, which makes optical axis alignment easy.

Moreover, preferably, the first lens, the wavelength-selecting material portion, and the second lens are integrated together into a single body.

According to the fluorescence analysis optical multiplexer/demultiplexer of the above embodiment, the first lens, the wavelength-selecting material portion, and the second lens are integrated together into a single body. As a result, the fluorescence analysis optical multiplexer/demultiplexer can be made to have a bonded together structure, and hence can be made compact.

To attain the above object, according to the present invention, there is provided a fluorescence analysis optical module comprising an exciting light source that outputs exciting light of dominant wavelength $\lambda_1$, a fluorescence analysis optical multiplexer/demultiplexer that carries out multiplexing/demultiplexing on fluorescence of dominant wavelength $\lambda_2$, wherein $\lambda_2 > \lambda_1$, emitted from a sample onto which the exciting light has been irradiated via a probe or an optical connector, a detector that receives the fluorescence transmitted through the fluorescence analysis optical multiplexer/demultiplexer, a first optical transmission line that connects the fluorescence analysis optical multiplexer/demultiplexer to the exciting light source, a second optical transmission line that connects the fluorescence analysis optical multiplexer/demultiplexer to the probe or the optical connector, and a third optical transmission line that connects the fluorescence analysis optical multiplexer/demultiplexer to the detector.

According to the fluorescence analysis optical module of the above embodiment, the fluorescence analysis optical module comprises an exciting light source that outputs exciting light of dominant wavelength $\lambda_1$, a fluorescence analysis optical multiplexer/demultiplexer that carries out multiplexing/demultiplexing on fluorescence of dominant wavelength $\lambda_2$, wherein $\lambda_2 > \lambda_1$, emitted from a sample onto which the exciting light has been irradiated via a probe or an optical connector, a detector that receives the fluorescence transmitted through the fluorescence analysis optical multiplexer/demultiplexer, a first optical transmission line that connects the fluorescence analysis optical multiplexer/demultiplexer to the exciting light source, a second optical transmission line that connects the fluorescence analysis optical multiplexer/demultiplexer to the probe or the optical connector, and a third optical transmission line that connects the fluorescence analysis optical multiplexer/demultiplexer to the detector. As a result, the exciting light can be led to the sample by the second optical transmission line, and the fluorescence from the sample can be led to the optical multiplexer/demultiplexer also by the second optical transmission line. The fluorescence analysis optical module can thus be made compact overall.

Moreover, preferably, the fluorescence analysis optical multiplexer/demultiplexer comprises a first lens that receives the exciting light and the fluorescence, and a wavelength-selecting material portion comprising a dielectric multilayer film that receives the exciting light and the fluorescence transmitted through the first lens, wherein the optical axis of the first optical transmission line is offset from the center of the optical axis of the first lens such that the angle of incidence of the exciting light onto the wavelength-selecting material portion is substantially not more than 5°.

According to the fluorescence analysis optical module of the above embodiment, the fluorescence analysis optical multiplexer/demultiplexer comprises a first lens that receives the exciting light and the fluorescence, and a wavelength-selecting material portion comprising a dielectric multilayer film that receives the exciting light and the fluorescence transmitted through the first lens, wherein the optical axis of the first optical transmission line is offset from the center of the optical axis of the first lens such that the angle of incidence of the exciting light onto the wavelength-selecting material portion is substantially not more than 5°. As a result, compared with a conventional optical system in which the exciting light is made to be incident on the wavelength-selecting material portion at an angle of incidence of 45°, the angle of incidence of the exciting light can be made very low, and hence transmission leakage for the exciting light, which comprises a mixture of a P wave and an S wave, can be kept down.

Moreover, preferably, each of the first optical transmission line, the second optical transmission line, and the third optical transmission line comprises an optical fiber.

According to the fluorescence analysis optical module of the above embodiment, each of the first optical transmission line, the second optical transmission line, and the third optical transmission line comprises an optical fiber. As a result, the fluorescence analysis optical module can be made simple, and small in size.

Moreover, preferably, each of the optical fibers is a single mode fiber.

Moreover, preferably, the fluorescence analysis optical module is constructed such that the probe has a fourth optical transmission line to which is connected another optical connector, and this other optical connector is connected to the optical connector.

According to the fluorescence analysis optical module of the above embodiment, the fluorescence analysis optical module is constructed such that the probe has a fourth optical transmission line to which is connected another optical connector, and this other optical connector is connected to the above-mentioned optical connector. As a result, a simple optical system can be constructed.

Moreover, preferably, the exciting light source has an optical modulation mechanism.

According to the fluorescence analysis optical module of the above embodiment, the exciting light source has an optical modulation mechanism. As a result, the detection sensitivity can be increased.

Moreover, preferably, the optical modulation mechanism is a lock-in modulation circuit that carries out lock-in in a range of 100 Hz to 10 KHz.

According to the fluorescence analysis optical module of the above embodiment, the optical modulation mechanism is a lock-in modulation circuit that carries out lock-in in a range of 100 Hz to 10 KHz. As a result, the detection sensitivity can be increased reliably.

Moreover, preferably, the lock-in modulation circuit carries out optical modulation on the exciting light source with a rectangular wave.

According to the fluorescence analysis optical module of the above embodiment, the lock-in modulation circuit carries out optical modulation on the exciting light source with a rectangular wave. As a result, the measurement accuracy can be further increased.

Moreover, preferably, an optical isolator is provided between the exciting light source and the fluorescence analysis optical multiplexer/demultiplexer.

According to the fluorescence analysis optical module of the above embodiment, an optical isolator is provided between the exciting light source and the fluorescence analysis optical multiplexer/demultiplexer. As a result, returning exciting light can be prevented from entering the exciting light source.

Moreover, preferably, an edge filter that does not transmit light of the dominant wavelength $\lambda_1$ is provided between the fluorescence analysis optical multiplexer/demultiplexer and the detector.

According to the fluorescence analysis optical module of the above embodiment, an edge filter that does not transmit light of the dominant wavelength $\lambda_1$, is provided between the fluorescence analysis optical multiplexer/demultiplexer and the detector. As a result, light outputted from the exciting light source can be reliably blocked from entering the detector.

Moreover, preferably, the above-mentioned fluorescence analyzer comprises a fluorescence analysis optical module as described above, a sample stage on which are mounted a plate-shaped element having therein a channel through which the sample is passed, and a moving mechanism that carries out positioning by relatively moving at least one of the sample stage and the fluorescence analysis optical module.

To attain the above object, according to the present invention, there is provided a fluorescence/photothermal conversion spectroscopic analyzer comprising a fluorescence analyzer as described above, a detecting light source that outputs detecting light of dominant wavelength $\lambda_3$, a photoelectric converter that detects a photothermal conversion signal intensity of the detecting light transmitted through a thermal lens produced in the sample by the exciting light, a photothermal conversion spectroscopic analysis optical multiplexer/demultiplexer that comprises a third lens, another wavelength-selecting material portion comprising a dielectric multilayer film, and a fourth lens arranged in this order, and a fifth optical transmission line that connects the photothermal conversion spectroscopic analysis optical multiplexer/demultiplexer to the detecting light source, wherein the photothermal conversion spectroscopic analysis optical multiplexer/demultiplexer is disposed at the midpoint of the third optical transmission line, the photothermal conversion spectroscopic analysis optical multiplexer/demultiplexer receives the detecting light from the detecting light source via the third lens, and the fluorescence transmitted through the other wavelength-selecting material portion is received by the detector via the fourth lens.

According to the fluorescence/photothermal conversion spectroscopic analyzer of the above embodiment, the fluorescence/photothermal conversion spectroscopic analyzer comprises a fluorescence analyzer as described above, a detecting light source that outputs detecting light of dominant wavelength $\lambda_3$, a photoelectric converter that detects a photothermal conversion signal intensity of the detecting light transmitted through a thermal lens produced in the sample by the exciting light, a photothermal conversion spectroscopic analysis optical multiplexer/demultiplexer that comprises a third lens, another wavelength-selecting material portion comprising a dielectric multilayer film, and a fourth lens arranged in this order, and a fifth optical transmission line that connects the photothermal conversion spectroscopic analysis optical multiplexer/demultiplexer to the detecting light source, wherein the photothermal conversion spectroscopic analysis optical multiplexer/demultiplexer is disposed at the midpoint of the third optical transmission line, the photothermal conversion spectroscopic analysis optical multiplexer/demultiplexer receives the detecting light from the detecting light source via the third lens, and the fluorescence transmitted through the other wavelength-selecting material portion is received by the detector via the fourth lens. As a result, by irradiating the exciting light source used in the fluorescence measurement onto the sample, fluorescence analysis and photothermal conversion spectroscopic analysis can be carried out simultaneously.

Moreover, preferably, the dominant wavelength $\lambda_3$ satisfies the relationship $\lambda_1 < \lambda_2 < \lambda_3$.

According to the fluorescence/photothermal conversion spectroscopic analyzer of the above embodiment, the dominant wavelength $\lambda_3$ satisfies the relationship $\lambda_1 < \lambda_2 < \lambda_3$. As a result, branching control of the detecting light by the optical multiplexer/demultiplexers can be carried out reliably.

Moreover, preferably, the difference between the dominant wavelength $\lambda_3$ and the dominant wavelength $\lambda_2$ is in a range of 50 to 500 nm, and the chromatic aberration in the thermal lens between the dominant wavelength $\lambda_1$ and the dominant wavelength $\lambda_3$ is in a range of 20 to 200 nm.

Moreover, preferably, the detecting light source has an optical modulation mechanism.

According to the fluorescence/photothermal conversion spectroscopic analyzer of the above embodiment, the detecting light source has an optical modulation mechanism. As a result, returning detecting light can be prevented from entering the detecting light source.

Moreover, preferably, the optical modulation mechanism is a lock-in modulation circuit that carries out lock-in in a range of 100 Hz to 10 KHz.

According to the fluorescence/photothermal conversion spectroscopic analyzer of the above embodiment, the optical modulation mechanism is a lock-in modulation circuit that carries out lock-in in a range of 100 Hz to 10 KHz. As a result, the amount of light can be made stable even if there is optical or electrical noise.

To attain the above object, according to the present invention, there is provided a fluorescence analysis chip comprising a plate-shaped element having therein a channel through which a sample is passed, the fluorescence analysis chip being disposed in a microchemical system having an irradiating device for irradiating exciting light onto the sample in the channel via a lens, and a detecting device for detecting outputted light from the sample in the channel, the fluorescence analysis chip characterized by having a reflecting mirror in or close to the channel, wherein the detecting device detects, via the lens, the outputted light containing fluorescence reflected by the reflecting mirror and condensed by the lens.

According to the fluorescence analysis chip of the above embodiment, the fluorescence analysis chip comprises a plate-shaped element having a reflecting mirror in or close to a channel through which a sample is passed for detecting outputted light upon irradiating with exciting light via a lens, wherein the outputted light containing fluorescence reflected by the reflecting mirror and condensed by the lens is detected via the lens. As a result, LIF analysis can be carried out easily and with high sensitivity.

Moreover, preferably, a surface of the channel onto which the exciting light is incident is flat, and another surface of the channel is curved.

According to the fluorescence analysis chip of the above embodiment, a surface of the channel onto which the exciting light is incident is flat, and another surface of the channel is curved. As a result, the reflecting mirror can be made to act as a condenser lens that condenses the fluorescence emitted from the sample in the channel, and hence LIF analysis can be carried out with higher sensitivity.

Moreover, preferably, the reflecting mirror condenses the fluorescence to a position where the exciting light is condensed by the lens.

According to the fluorescence analysis chip of the above embodiment, the reflecting mirror condenses the fluorescence to a position where the exciting light is condensed by the lens. As a result, the condensed fluorescence enters the lens reliably, whereby LIF analysis can be carried out with yet higher sensitivity.

Moreover, preferably, the reflecting mirror is a metal film.

According to the fluorescence analysis chip of the above embodiment, the reflecting mirror is a metal film. As a result, the reflectance can be made to be high over a broad wavelength range in the visible region, and hence LIF analysis can be carried out with yet higher sensitivity.

Moreover, preferably, the plate-shaped element comprise a first plate-shaped element having therein a groove constituting the channel, and a second plate-shaped element bonded to a groove-side surface of the first plate-shaped element, wherein the reflecting mirror is on a surface of the first plate-shaped element on the opposite side to the groove-side surface.

According to the fluorescence analysis chip of the above embodiment, the plate-shaped element comprise a first plate-shaped element having therein a groove constituting the channel, and a second plate-shaped element bonded to a groove-side surface of the first plate-shaped element, wherein the reflecting mirror is on a surface of the first plate-shaped element on the opposite side to the groove-side surface. As a result, the fluorescence emitted from the sample in the channel can be reliably detected via the lens through which the exciting light is irradiated, and hence LIF analysis can be carried out with higher sensitivity.

Moreover, preferably, the plate-shaped element comprises a first plate-shaped element having therein a slit constituting the channel, and two second plate-shaped elements bonded respectively to the two surfaces of the first plate-shaped element, wherein the reflecting mirror is on surfaces of the slit, and between the first plate-shaped element and the one of the second plate-shaped elements that is bonded to the surface of the first plate-shaped element on the opposite side to the slit-side surface.

According to the fluorescence analysis chip of the above embodiment, the plate-shaped element comprises a first plate-shaped element having therein a slit constituting the channel, and two second plate-shaped elements bonded respectively to the two surfaces of the first plate-shaped element, wherein the reflecting mirror is on surfaces of the slit, and between the first plate-shaped element and the one of the second plate-shaped elements that is bonded to the surface of the first plate-shaped element on the opposite side to the slit-side surface. As a result, the fluorescence emitted from the sample in the channel can be reliably detected via the lens through which the exciting light is irradiated, and hence LIF analysis can be carried out with higher sensitivity.

Moreover, preferably, the plate-shaped element has therein segmenting channels for subjecting the sample to electrophoresis, and a separating channel that intersects with the segmenting channels, wherein the reflecting mirror is in a region of the separating channel from which the fluorescence emitted from the sample is led out.

BRIEF DESCRIPTION OF THE DRAWINGS

FIG. 6A is a schematic view showing light being incident on the filter 501;

FIG. 6B shows the relationship between transmittance and wavelength for a P wave and an S wave when the angle of incidence is 45°; and FIG. 6C shows the relationship between transmittance and wavelength for the P wave and the S wave when the angle of incidence is 0°;

FIG. 8A shows the transmission characteristics in the case of a long pass filter;

FIG. 8B shows the transmission characteristics in the case of a band pass filter; and FIG. 8C shows the transmission characteristics in the case of a short pass filter;

FIG. 10A is a perspective view of plate-shaped element constituting the fluorescence analysis chip 20; and FIG. 10B is a sectional view of the fluorescence analysis chip 20 taken through plane A-A.

BEST MODE FOR CARRYING OUT THE INVENTION

Embodiments of the present invention will now be described in detail with reference to the drawings.

Figure 1:
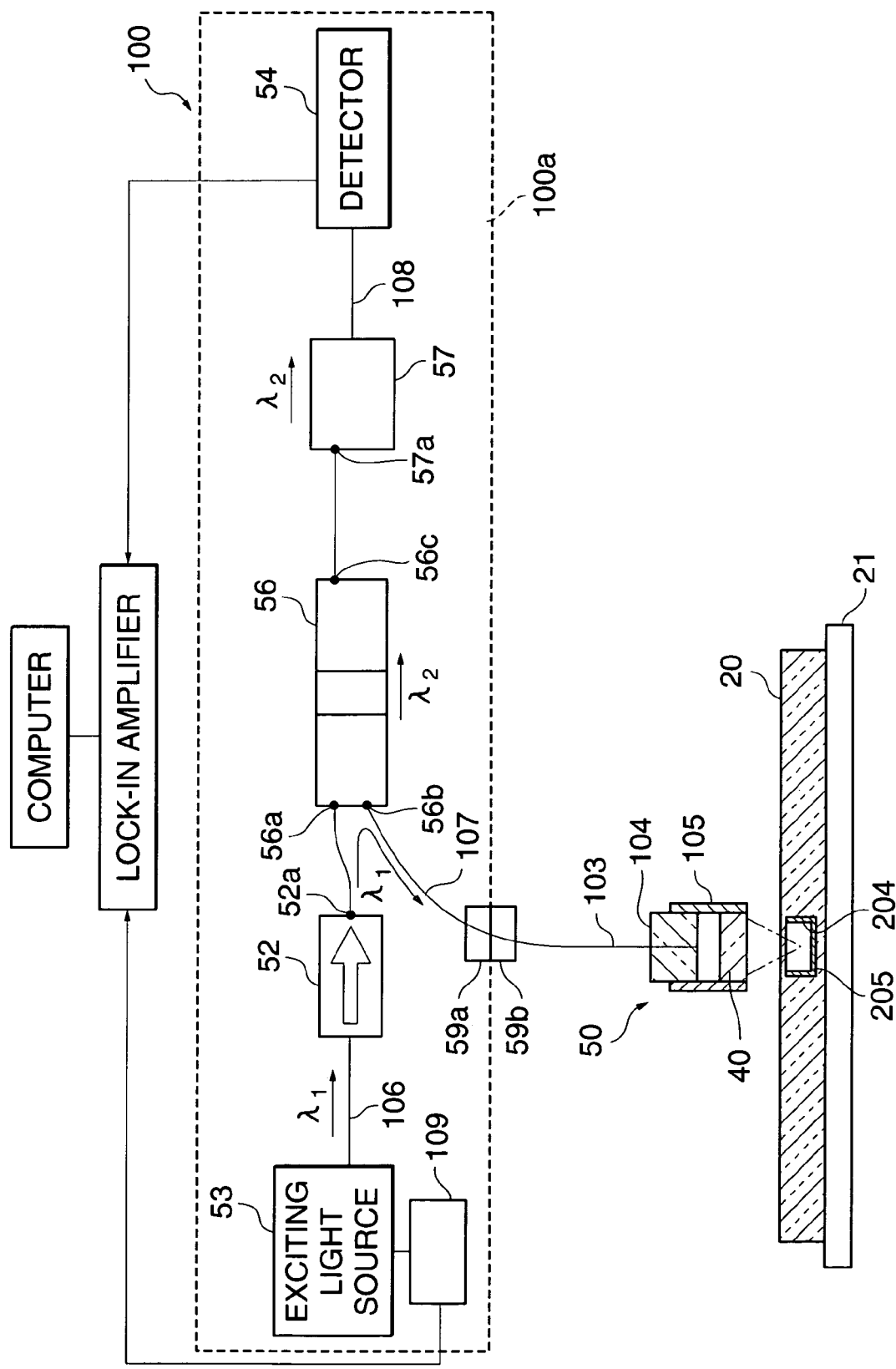
FIG. 1 is a view schematically showing the construction of a microchemical system, which is a fluorescence analyzer according to an embodiment of the present invention.

FIG. 1 is a view schematically showing the construction of a microchemical system, which is a fluorescence analyzer according to an embodiment of the present invention.

As shown in FIG. 1, the microchemical system 100 is comprised of a fluorescence analysis optical module 100a, a lens-possessing optical fiber (hereinafter referred to as a "probe") 50 that condenses exciting light onto a sample solution in a channel 204 inside a fluorescence analysis chip 20, and a sample stage 21 on which the fluorescence analysis chip 20 is mounted.

The sample stage 21 has a moving mechanism, not shown, that positions the sample by moving the sample stage 21 relative to the probe 50. Although the sample stage 21 has such a moving mechanism in the present embodiment, so long as positioning of the sample can be carried out, there is no limitation to this, but rather the probe 50 may instead have a moving mechanism that moves the probe 50 relative to the sample stage 21.

The fluorescence analysis optical module 10a is comprised of an exciting light source 53 that outputs the exciting light which is of dominant wavelength $\lambda_1$, a fluorescence analysis optical multiplexer/demultiplexer 56 for the fluorescence analyzer which analyzes fluorescence of dominant wavelength $\lambda_2$ (wherein $\lambda_2 > \lambda_1$) emitted from the sample upon the exciting light being irradiated onto the sample via the probe 50, a detector 54 that receives the fluorescence, an optical fiber 106 (first optical transmission line) that connects the exciting light source 53 and the fluorescence analysis optical multiplexer/demultiplexer 56 together, an optical fiber 107 (second optical transmission line) that connects the probe 50 and the fluorescence analysis optical multiplexer/demultiplexer 56 together, and an optical fiber 108 (third optical transmission line) that connects the detector 54 and the fluorescence analysis optical multiplexer/demultiplexer 56 together. By giving the fluorescence analysis optical module 100a such a construction, the exciting light can be led to the sample by the optical fiber 107, and the fluorescence from the sample can be led to the fluorescence analysis optical multiplexer/demultiplexer 56 also by the optical fiber 107. The fluorescence analysis optical module 100a can thus be made compact overall.

The optical fiber 107 is connected to the fluorescence analysis optical multiplexer/demultiplexer 56 directly, but is detachably connected to the probe 50 via connectors. Specifically, the optical fiber 107 has a connector 59a at a leading end thereof, and an optical fiber 103 of the probe 50 has a connector 59b at a leading end thereof. The probe 50 and the fluorescence analysis optical multiplexer/demultiplexer 56 are connected together by connecting the connector 59a to the connector 59b. As a result, a simple optical system can be constructed.

The optical fiber 106 may have therein an isolator 52 for which the loss for light entering from an output terminal 52a side thereof is high at not less than 30 dB. As a result, exciting light of wavelength $\lambda_1$ returning from the fluorescence analysis optical multiplexer/demultiplexer 56 can be prevented from entering the exciting light source 53.

Moreover, the optical fiber 108 may have therein an edge filter 57 having a cutoff wavelength $\lambda'$ wherein $\lambda_1 < \lambda' < \lambda_2$. As a result, the fluorescence emitted by the sample in the channel 204 can be led to the detector 54 while reliably preventing exciting light from entering the detector 54; and hence LIF analysis can be carried out with higher sensitivity.

As described above, in the fluorescence analysis optical module 100a, optical fibers 103, 106, 107 and 108 are used for transmitting light between the devices described above that together constitute the module. The module can thus be made simple, and small in size.

The probe 50 is comprised of the optical fiber 103, which is a single mode optical fiber one end of which is connected to the connector 59b, a ferrule 104 that holds a tip portion at the other end of the optical fiber 103, an irradiating lens 40 that is connected to the tip portion of the optical fiber 103, and a tube 105 that fixes the ferrule 104 and the irradiating lens 40 in place. The irradiating lens 40 is comprised of a rod lens.

The exciting light source 53 is connected to a lock-in modulation circuit 109, and lock-in in a range of 100 Hz to 10 KHz is carried out by the lock-in modulation circuit 109. As a result, the detection sensitivity can be increased reliably.

The lock-in modulation circuit 109 carries out optical modulation on the exciting light source 53 with a rectangular wave. As a result, the measurement accuracy can be further increased.

In the present embodiment, a lock-in modulation circuit 109 is used. However, so long as there is an optical modulation mechanism enabling the detection sensitivity to be increased, there is no limitation to such a lock-in modulation circuit.

Moreover, in FIG. 1, the fluorescence analysis optical multiplexer/demultiplexer 56 and the probe 50 are detachably connected together using the connectors 59a and 59b.

However, there is no limitation thereto, but rather, the fluorescence analysis optical multiplexer/demultiplexer 56 and the probe 50 may, for example, be connected directly together by an optical fiber, or may be fused together.

Figure 2:
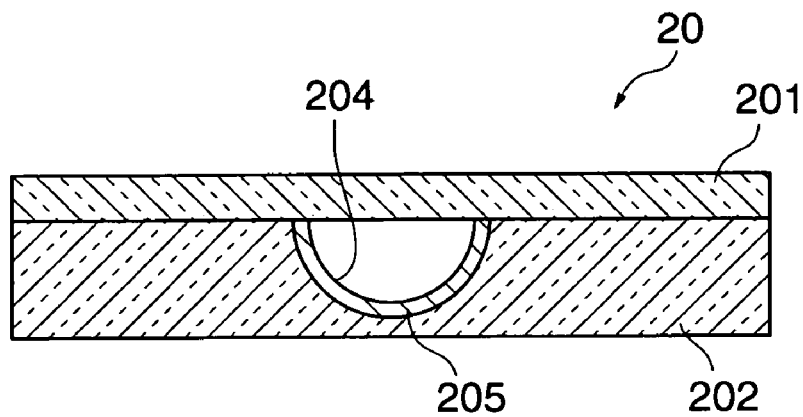
FIG. 2 is a schematic view of a fluorescence analysis chip 20 appearing in FIG. 1.

FIG. 2 is a schematic view of the fluorescence analysis chip 20 appearing in FIG. 1

As shown in FIG. 2, the fluorescence analysis chip 20 is comprised of two glass substrates 201 and 202 bonded on top of one another. The channel 204, through which the sample is passed when carrying out mixing, agitation, synthesis, separation, extraction, detection or the like, is formed in the glass substrate 202.

The channel 204 is formed so as to have a curved surface by etching, and is coated with a reflective metal film 205 made of aluminum, chromium, nickel, palladium or the like. As a result, the channel 204 carries out a function of a condenser lens that condenses the fluorescence emitted from the sample in the channel 204, and hence highly sensitive LIF analysis can be carried out. Moreover, if the shape of the channel 204 and the coating with the reflective metal film 205 are made to be such that the position to which the fluorescence is condensed is the focal position of the exciting light, then the condensed fluorescence will enter the probe 50 reliably, whereby the LIF analysis can be carried out with yet higher sensitivity.

As the coating, specifically, a film of aluminum, palladium or the like is formed through vacuum deposition, sputtering or the like on a portion of the surface 202a of the glass substrate 202 where the channel 204 is formed, and then a photoresist is applied on, exposure with light, developing, etching, and removal of the photoresist are carried out with a photomask disposed over the channel 204. As a result, coating with the reflective metal film 205 can be carried out reliably even in the case that the channel 204 is very fine.

From the standpoint of durability and chemical resistance, the material of the fluorescence analysis chip 20 is preferably a glass, and considering usage with biological samples such as cell samples, for example in DNA analysis, a glass having high acid resistance and alkali resistance is preferable, specifically a borosilicate glass, a soda lime glass, an aluminoborosilicate glass, a quartz glass or the like. However, if the usage is limited accordingly, then an organic material such as a plastic may be used.

Furthermore, examples of adhesives that can be used to bond the glass substrates 201 and 202 together include organic adhesives such as acrylic adhesives and epoxy adhesives, and inorganic adhesives; the adhesive may be, for example, an ultraviolet-curing type, a thermosetting type, or a two-liquid-curing type. Alternatively, the glass substrates 201 and 202 may be fused together by heat fusion.

Figure 3:
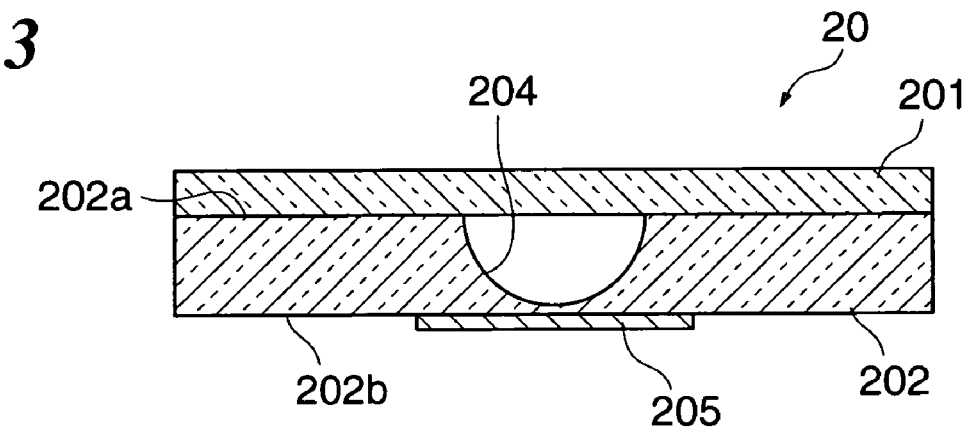
FIG. 3 is a schematic view of a variation of the fluorescence analysis chip 20 appearing in FIG. 1.

Moreover, instead of coating the channel 204 with the reflective metal film 205, such a reflective metal film 205 may instead be formed by vapor deposition on a surface 202b of the glass substrate 202 on the opposite side to the surface 202a so as to reflect all light that is irradiated into the channel 204 and transmitted through the glass substrate 202 (see FIG. 3). As a result, highly sensitive LIF analysis can be carried out.

Figure 4:
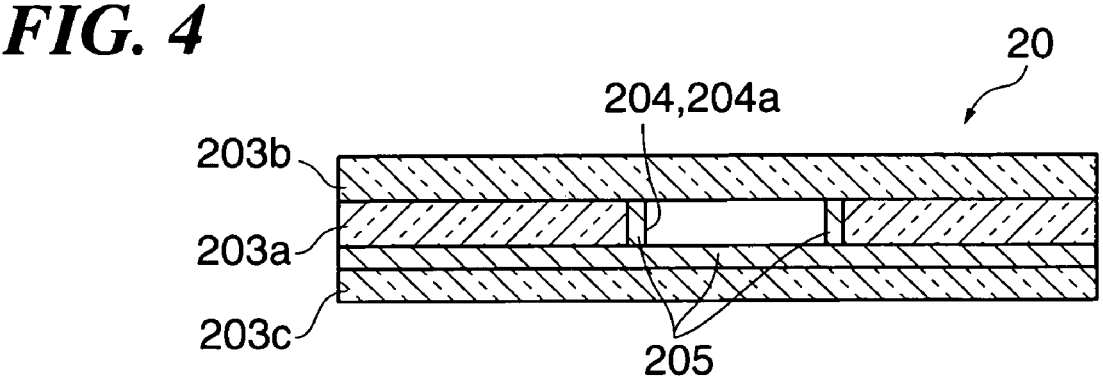
FIG. 4 is a schematic view of a variation of the fluorescence analysis chip 20 appearing in FIG. 1.

Moreover, a construction may also be adopted in which the fluorescence analysis chip 20 is comprised of two glass substrates 203b and 203c, and bonded therebetween, a glass substrate 203a having therein a slit 204a in the form of the channel 204, surfaces of the slit 204a being coated with a reflective metal film 205 by vapor deposition or the like, and moreover a surface of the glass substrate 203c that is bonded to the glass substrate 203a being coated with a reflective metal film 205 (see FIG. 4). According to such an embodiment, highly sensitive LIF analysis can again be carried out.

Although a fluorescence analysis chip 20 coated with a reflective metal film 205 as described above is used in the present embodiment, LIF analysis can be carried out even if a fluorescence analysis chip 20a not coated with a reflective metal film 205 is used, although in that case the detected fluorescence will be weak.

Figure 5:
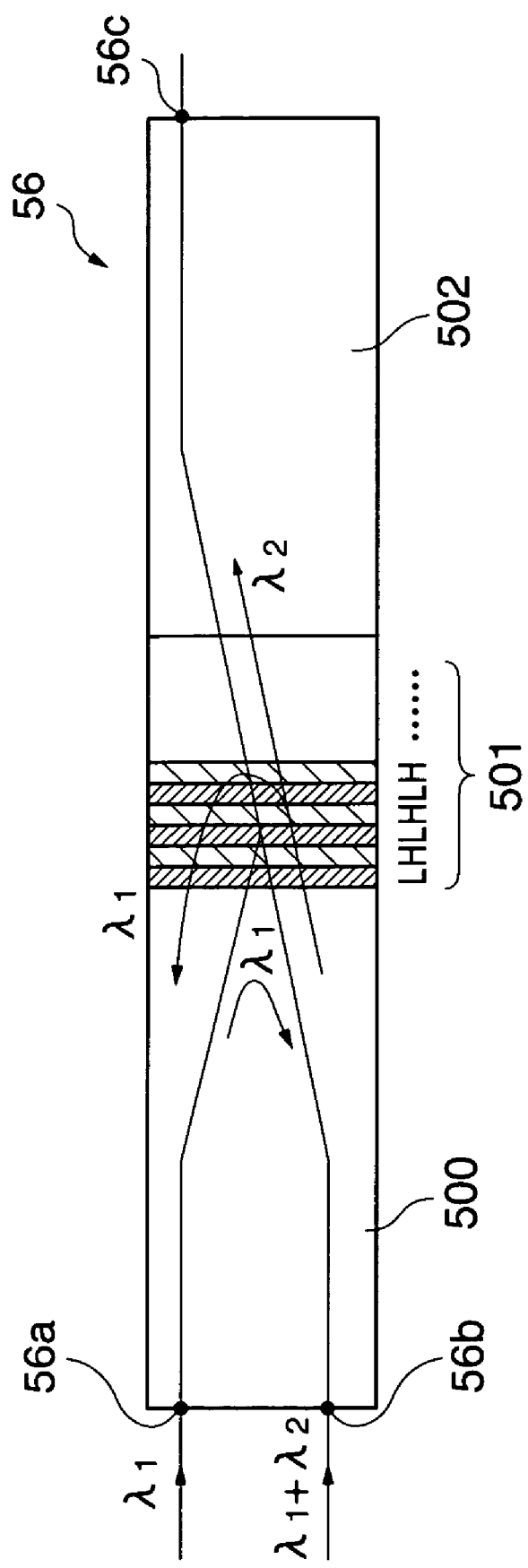
FIG. 5 is a schematic sectional view of a fluorescence analysis optical multiplexer/demultiplexer 56 appearing in FIG. 1.

FIG. 5 is a schematic sectional view of the fluorescence analysis optical multiplexer/demultiplexer 56 appearing in FIG. 1.

As shown in FIG. 5, the fluorescence analysis optical multiplexer/demultiplexer 56 is comprised of a rod lens 500 (first lens), a filter 501 (wavelength-selecting material portion: filter-on-lens type) formed by vapor deposition on the rod lens 500, and a rod lens 502 (second lens) fixed to the filter 501 by an adhesive, the rod lens 500, the filter 501 and the rod lens 502 being arranged in series in this order from an end of the fluorescence analysis optical multiplexer/demultiplexer 56 where there are output terminals 56a and 56b, and being integrated together into a single body. As a result, the fluorescence analysis optical multiplexer/demultiplexer 56 can be made to have a bonded together structure, and hence can be made compact. The filter 501 may alternatively be formed on a glass substrate, the glass substrate being disposed between the rod lens 500 and the rod lens 502.

The filter 501 is a dielectric multilayer film in which a plurality of layers (L) made of $SiO_2$ or the like having a low refractive index and layers (H) made of $TiO_2$, $ZrO_2$, $Ta_2O_5$ or the like having a high refractive index are formed on one another, and is a so-called long pass filter for which the transmittance of light of wavelength shorter than a cutoff wavelength $\lambda$ (wherein $\lambda_1 < \lambda < \lambda_2$) entering from either of the output terminals 56a and 56b of the fluorescence analysis optical multiplexer/demultiplexer 56 is not more than $-30$ dB (0.1%), and the transmittance of light of wavelength longer than $\lambda$ is not less than $-3$ dB (97 to 50%). As a result, light outputted from the exciting light source 53 can be reliably blocked from entering the detector 54.

Due to the above, the exciting light of dominant wavelength $\lambda_1$ entering from the output terminal 56a is reflected by the filter 501 due to the transmittance of the filter 501 to this light being not more than $-30$ dB, and thus led to the other output terminal 56b. As a result, the exciting light can be reliably prevented from being transmitted through the fluorescence analysis optical multiplexer/demultiplexer 56, and hence the measurement/detection noise level for $\lambda_2$ can be effectively reduced.

On the other hand, light led to the output terminal 56b via the probe 50 is comprised of exciting light of dominant wavelength $\lambda_1$, and fluorescence of dominant 2.5 wavelength $\lambda_2$ emitted from the sample, both of which are reflected by the reflective metal film 205. Of these light, the exciting light is reflected by the filter 501 as for the exciting light from the exciting light source 53 described above, and thus led to the output terminal 56a, whereas the fluorescence is transmitted through the filter 501 due to the transmittance of the filter 501 to this light being not less than $-3$ dB, and thus led to an input terminal 56c. As a result, good detection signal intensity for the fluorescence transmitted through the fluorescence analysis optical multiplexer/demultiplexer 56 can be secured. The filter 501 may alternatively be a holograph.

That is, by making the filter 501 used in the fluorescence analysis optical multiplexer/demultiplexer 56 be a long pass filter that cuts short wavelengths and passes long wavelengths, the transmission loss for the exciting light, which would cause noise in the fluorescence measurement if transmitted through the filter 501 so as to reach the detector 54, can be effectively increased, and moreover the exciting light is reflected by the filter 501, and hence a good amount of exciting light being irradiated onto the sample can be secured.

Each of the rod lenses 500 and 502 is a cylindrical gradient index rod lens provided with a refractive index gradient such that the refractive index decreases from the center of the lens outward. As a result, each of the end faces, i.e. the input face and the output face, of each of the rod lenses 500 and 502 is a flat face perpendicular to the optical axis, and hence assembly such as joining the lenses together can be carried out easily. Moreover, because each of the rod lenses 500 and 502 is cylindrical, the rod lenses 500 and 502 can easily be housed in a cylindrical holder, which makes optical axis alignment easy.

Due to the fluorescence analysis optical multiplexer/demultiplexer 56 having the construction described above, the fluorescence can be led to the detector while effectively preventing exciting light from entering the detector and thus causing noise in the detection.

Figure 6A:
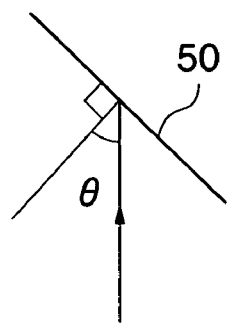
FIGS. 6A, 6B and 6C are diagrams useful in explaining optical transmission characteristics of a filter 501; specifically.
Figure 6B:
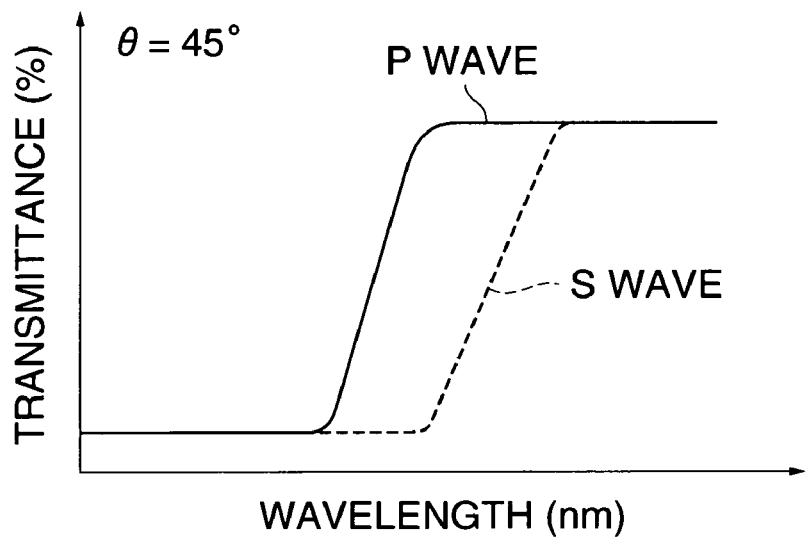
Figure 6C:
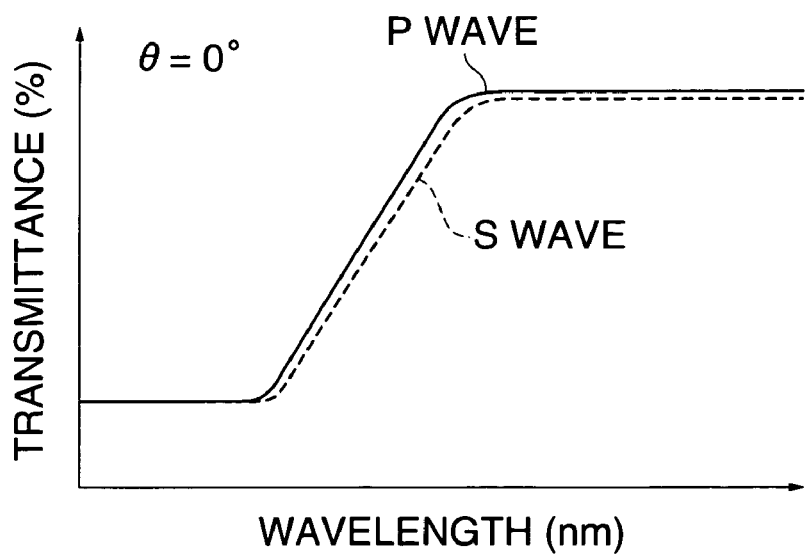

Moreover, as shown in FIG. 6, the filter 501 has a characteristic that the greater the angle of incidence θ of the light led in (see FIG. 6A), the greater the difference in transmittance close to the cutoff wavelength between a P wave and an S wave constituting natural light (see FIGS. 6B and 6C), and hence the broader the boundary between the reflected wavelength band and the transmitted wavelength band for natural light. However, as shown in FIG. 5, the construction is such that the angle of incidence for light led in from the output terminal 56a or 56b is substantially not more than 5°, and hence transmission leakage for the exciting light, which is comprised of a mixture of a P wave and an S wave, can be kept down. That is, the exciting light, which has a relatively high intensity compared with the intensity of the fluorescence emitted from the sample, can be effectively prevented from being transmitted through the filter 501, and hence noise when detecting the fluorescence can be reduced.

Figure 7:
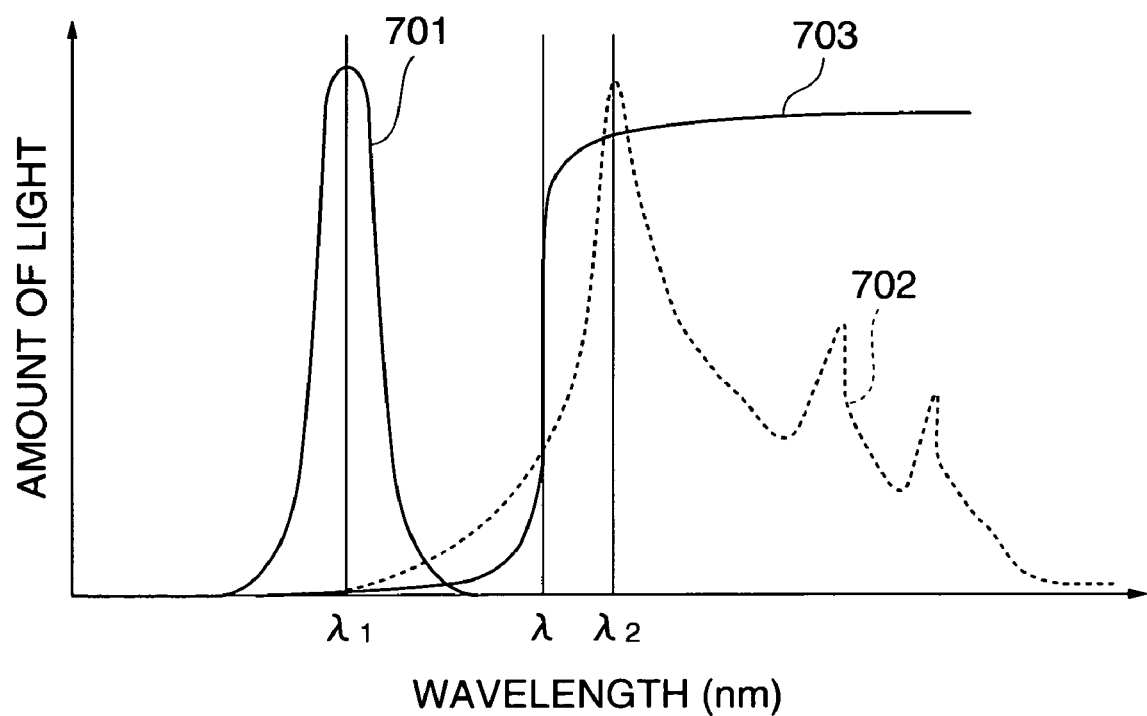
FIG. 7 is a graph showing spectra of exciting light and fluorescence, and transmission characteristics of a filter 501.

In particular, as shown in FIG. 7, in the case that the wavelength region between the dominant wavelength $\lambda_1$ of the exciting light and the dominant wavelength $\lambda_2$ of the fluorescence is narrow, the exciting light can be cut reliably, and hence the fluorescence detection characteristics can be improved reliably.

As described above, it is most preferable to use a long pass filter as the filter 501. To show the reason for this, a description will now be given of problems that arise in the case of using other wavelength-selecting filters as the filter 501.

Figure 8A:
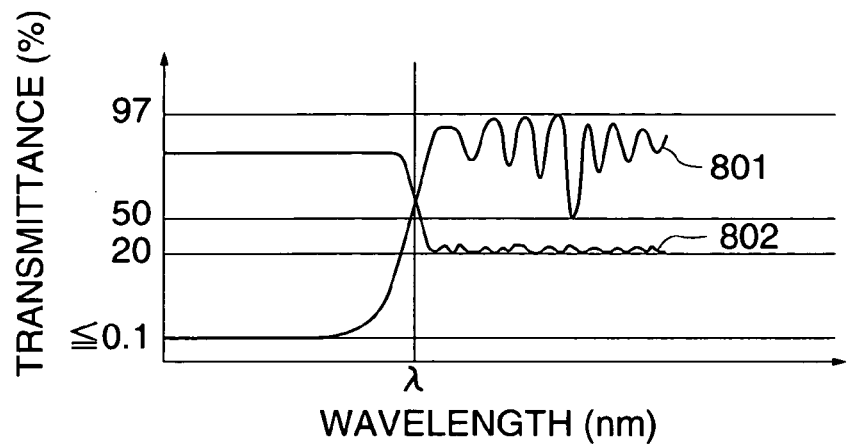
FIGS. 8A, 8B and 8C are graphs showing transmission characteristics of a filter 501; specifically.

Other than a long pass filter as described above, a band pass filter that transmits only light in a specified wavelength band, and a short pass filter that, conversely to a long pass filter, has a transmittance to light of wavelength longer than a cutoff wavelength λ of −30 to −50 dB, and a transmittance to light of wavelength shorter than λ of not less than −3 dB (97 to 50%) are also known as wavelength-selecting filters as shown in FIG. 8.

Figure 8B:
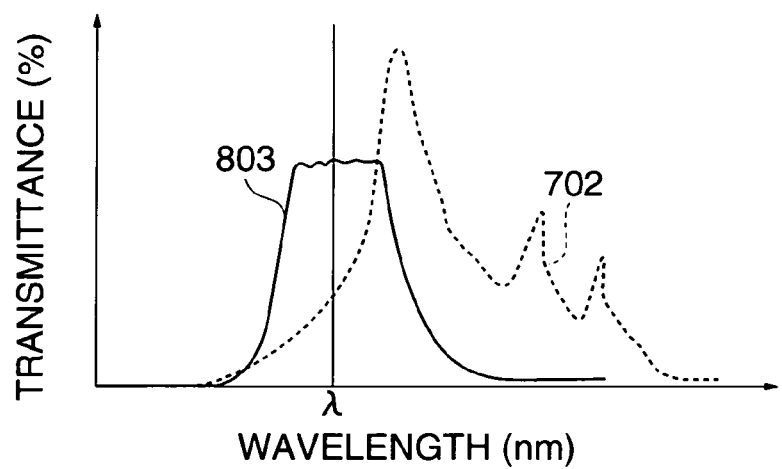

Here, if a band pass filter is used as the filter 501, then as shown in FIG. 8B, it inevitably becomes that all of fluorescence 702 from a sample with a broad emission spectrum is no longer transmitted, and manufacture is difficult in terms of technology and cost. There is thus a problem that the measurement sensitivity drops.

Figure 8C:
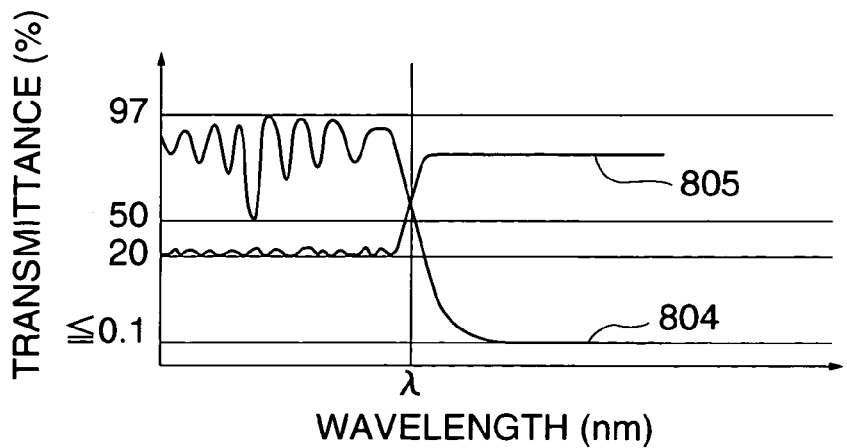

On the other hand, if a short pass filter is used, then a construction must be adopted in which the probe 50 is installed on the side of transmission through the filter 501, and the detector 54 is installed on the side of reflection from the probe 50. However, as shown in FIG. 8C, the transmittance (805) of the short pass filter to returning exciting light is not less than −20 dB (approximately 1%), and hence there is a problem that returning exciting light may enter the detector 54.

Next, a fluorescence/photothermal conversion spectroscopic analyzer according to an embodiment of the present invention will be described.

Figure 9:
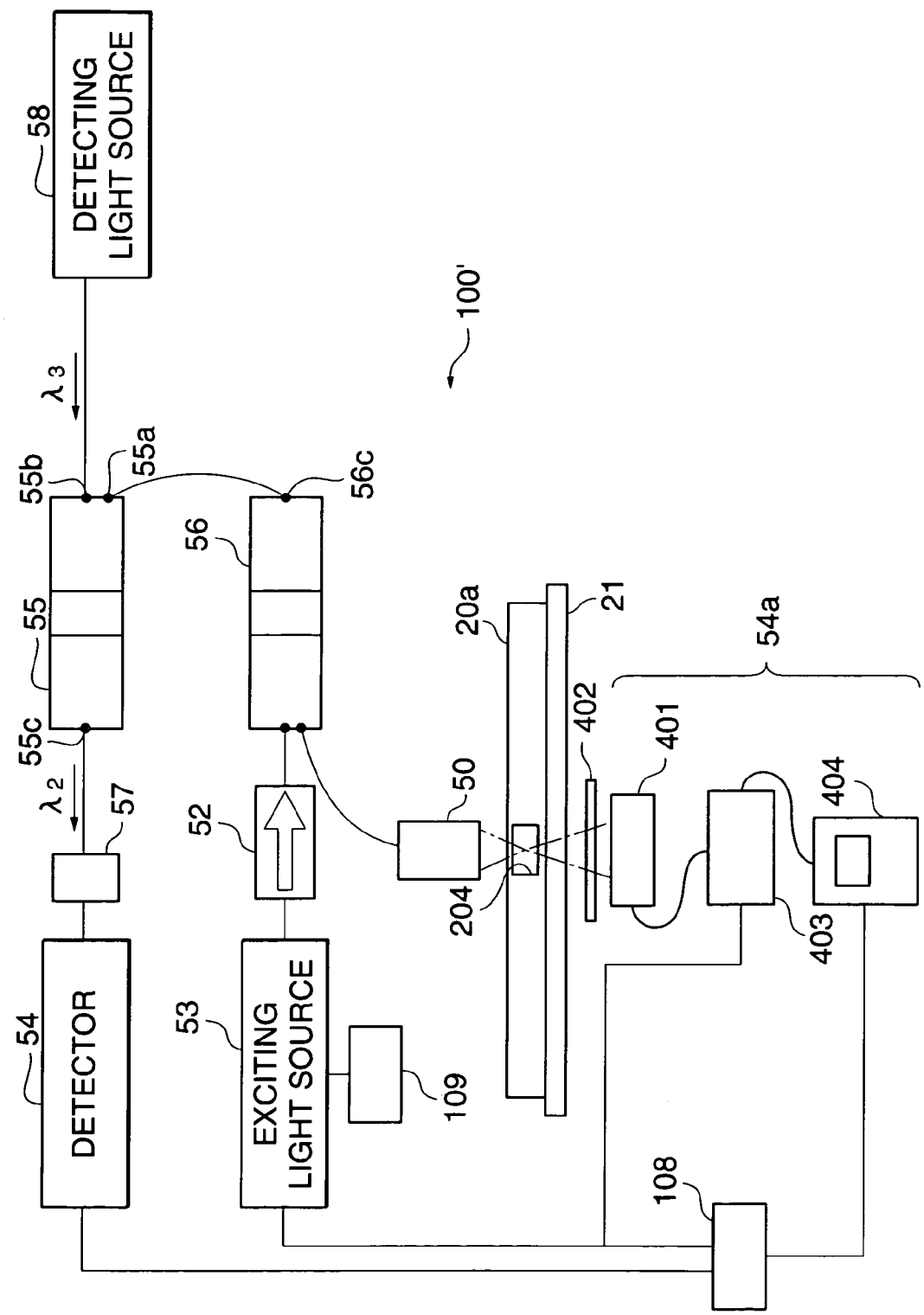
FIG. 9 is view schematically showing the construction of a microchemical system, which is a fluorescence/photothermal conversion spectroscopic analyzer according to an embodiment of the present invention.

FIG. 9 is view schematically showing the construction of a microchemical system, which is a fluorescence/photothermal conversion spectroscopic analyzer according to an embodiment of the present invention.

As shown in FIG. 9, the microchemical system 100' is a variation of the microchemical system 100, functioning not only as a fluorescence analyzer, but also as a photothermal conversion spectroscopic analyzer that measures photothermal conversion signal intensity. The construction of the present variation is fundamentally similar to that of the microchemical system 100, and hence component elements that are the same as ones in the microchemical system 100 are designated by the same reference numerals, and description thereof will be omitted here.

As shown in FIG. 9, beyond the construction possessed by the microchemical system 100, the microchemical system 100' uses a fluorescence analysis chip 20a not coated with a reflective metal film 205 instead of the fluorescence analysis chip 20. Moreover, the microchemical system 100' has a detecting light source 58 that outputs detecting light of wavelength $\lambda_3$, a light-receiving section 54a that receives outputted light from the microchemical system chip 20a, and a photothermal conversion spectroscopic analysis optical multiplexer/demultiplexer 55. Similar to the fluorescence analysis optical multiplexer/demultiplexer 56, the photothermal conversion spectroscopic analysis optical multiplexer/demultiplexer 55 has input terminals 55a and 55b of a third lens, and an output terminal 55c of a fourth lens. A dielectric multilayer film constituting a wavelength-selecting material portion provided between the third lens and the fourth lens is preferably a filter (short pass filter) that reflects at the wavelength $\lambda_3$ of the detecting light source entering from the third lens, and transmits at the dominant wavelength $\lambda_2$ (wherein $\lambda_2<\lambda_3$) of the fluorescence emitted from the sample, since then a signal having little noise is obtained from the weak fluorescence.

Furthermore, for the photothermal conversion spectroscopic analysis optical multiplexer/demultiplexer 55, the input terminals 55a and 55b are connected by optical fibers to the input terminal 56c of the fluorescence analysis optical multiplexer/demultiplexer 56 and the detecting light source 58 respectively, and the output terminal 55c on the opposite side is connected by an optical fiber to the detector 54.

Here, to prevent the sample from emitting fluorescence or forming a thermal lens due to being irradiated by the detecting light, the dominant wavelength $\lambda_3$ of the detecting light is generally set to be longer than the dominant wavelength $\lambda_1$ of the exciting light. In the present embodiment, the dominant wavelength $\lambda_3$ of the detecting light is further set to be longer than the dominant wavelength $\lambda_2$ of the fluorescence. Specifically, the difference between $\lambda_3$ and $\lambda_2$ is made to be in a range of 50 to 500 nm, and the chromatic aberration in the thermal lens between $\lambda_1$ and $\lambda_3$ is made to be in a range of 20 to 200 nm. As a result, branching control of the detecting light by the fluorescence analysis optical multiplexer/demultiplexer 56 can be carried out reliably.

The light-receiving section 54a is comprised of a wavelength filter 402 that selectively filters therethrough only the detecting light, a photoelectric converter 401 that detects the amount of detecting light filtered through by the wavelength filter 402, a lock-in amplifier 403 that is connected to the photoelectric converter 401 and a modulator 109, and synchronizes a signal from the photoelectric converter 401 with the modulator 109, and a computer 404 that analyzes the signal. The computer 404 is connected to the lock-in amplifier 403. The modulator 109 carries out lock-in on the detecting light in a range of 100 Hz to 10 KHz. As a result, the amount of light can be made stable even if there is optical or electrical noise.

The probe 50 condenses not only the exciting light from the exciting light source 53, but also the detecting light from the detecting light source 58, onto the sample solution in the channel 204 inside the fluorescence analysis chip 20a. Because the fluorescence analysis chip 20a does not have a reflective metal film 205, the detecting light irradiated before and after thermal lens formation is transmitted through the fluorescence analysis chip 20a. On the other hand, in the case that fluorescence is emitted from the sample, because the fluorescence is emitted from the sample isotropically, the probe 50 leads the fluorescence to the fluorescence analysis optical multiplexer/demultiplexer 56.

The light-receiving section 54a is disposed in a position on the opposite side of the fluorescence analysis chip 20a to the probe 50. Of the exciting light and the detecting light transmitted through the fluorescence analysis chip 20a, only the detecting light is selectively filtered through by the wavelength filter 402, and then the amount of detecting light that has been filtered through is detected by the photoelectric converter 401, and a detection signal from the photoelectric converter 401 is sent to the lock-in amplifier 403.

For the photothermal conversion spectroscopic analysis optical multiplexer/demultiplexer 55, the input terminals 55a and 55b are connected to the input terminal 56c of the fluorescence analysis optical multiplexer/demultiplexer 56 by a detecting light source-possessing optical fiber, and the output terminal 55c on the opposite side is connected to the detector 54 by an optical fiber.

Next, an electrophoretic separation spectrum measuring apparatus using the microchemical system 100 of FIG. 1 will be described.

Figure 10A:
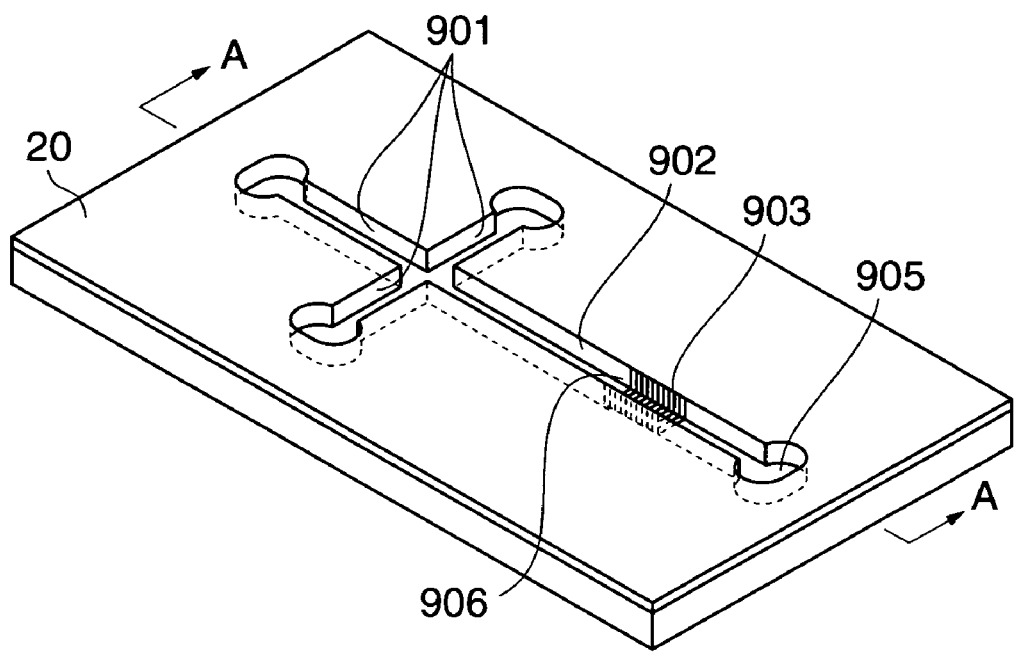
FIGS. 10A and 10B are views schematically showing the structure of a fluorescence analysis chip 20 appearing in FIG. 1; specifically.
Figure 10B:
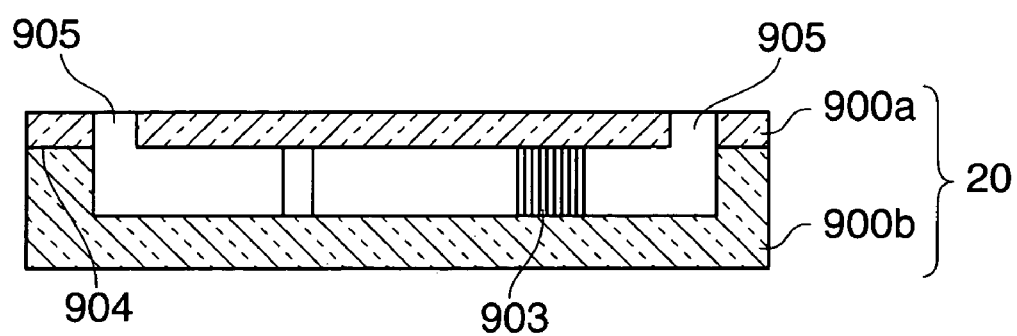

FIG. 10 are views schematically showing the structure of a fluorescence analysis chip 20 appearing in FIG. 1. Specifically, FIG. 10A is a perspective view of plate-shaped element constituting the fluorescence analysis chip 20, and FIG. 10B is a sectional view of the fluorescence analysis chip 20 taken through plane A-A.

As shown in FIG. 10, the fluorescence analysis chip 20 is comprised of a base plate 900b having formed in one surface thereof (hereinafter referred to as the "joining surface 904") segmenting channels 901 of width 0.3±0.2 mm that form three branches and a separation analysis channel 902 that is connected to the segmenting channels 901, and a cover plate 900a that is joined to the joining surface 904 of the base plate 900b. The cover plate 900a has therein four through holes 905 for sample introduction/discharge in positions corresponding to the segmenting channels 901 and the separation analysis channel 902.

The separation analysis channel 902 has therein an analysis section 906 that is coated with a reflective metal film 903 made of aluminum. Exciting light of dominant wavelength 658 nm and detecting light of dominant wavelength 780 nm are condensed by the probe 50 into the analysis section 906.

By adopting such a chip construction, the resolution of an electrophoretic separation spectrum can be improved.

INDUSTRIAL APPLICABILITY

As described in detail above, according to a fluorescence analysis optical multiplexer/demultiplexer of the present invention, the fluorescence analysis optical multiplexer/demultiplexer is for use in a fluorescence analyzer that analyzes fluorescence of dominant wavelength $\lambda_2$ emitted from a sample onto which has been irradiated exciting light of dominant wavelength $\lambda_1$, wherein $\lambda_2 > \lambda_1$, and is comprised of a first lens that receives the exciting light and the fluorescence, a wavelength-selecting material portion comprised of a dielectric multilayer film that receives the exciting light and the fluorescence transmitted through the first lens, and a second lens that receives the fluorescence transmitted through the wavelength-selecting material portion. As a result, the exciting light, which has a relatively high intensity compared with the intensity of the fluorescence emitted from the sample, can be effectively blocked, and hence noise when detecting the fluorescence can be reduced. LIF analysis can thus be carried out easily and with high sensitivity.

According to the fluorescence analysis optical multiplexer/demultiplexer of an embodiment, the dielectric multilayer film is a long pass filter having a cutoff wavelength between the dominant wavelength $\lambda_1$ and the dominant wavelength $\lambda_2$. As a result, the transmission loss for the exciting light, which would cause noise in the fluorescence measurement if transmitted through the wavelength-selecting material portion so as to reach a detector for the fluorescence, can be effectively increased, and moreover the exciting light is reflected by the wavelength-selecting material portion, and hence a good amount of exciting light being irradiated onto the sample can be secured.

According to the fluorescence analysis optical multiplexer/demultiplexer of an embodiment, the transmittance of the wavelength-selecting material portion to light of the dominant wavelength $\lambda_1$ is not more than −30 dB. As a result, even if the number of layers formed on one another in the dielectric multilayer film is low, the exciting light can be reliably prevented from being transmitted through the fluorescence analysis optical multiplexer/demultiplexer, and hence the measurement/detection noise level for $\lambda_2$ can be effectively reduced.

According to the fluorescence analysis optical multiplexer/demultiplexer of an embodiment, the transmittance of the wavelength-selecting material portion to light of the dominant wavelength $\lambda_2$ emitted from the sample is not less than −3 dB. As a result, good detection signal intensity for the fluorescence transmitted through the fluorescence analysis optical multiplexer/demultiplexer can be secured.

According to the fluorescence analysis optical multiplexer/demultiplexer of an embodiment, each of the first lens and the second lens is a cylindrical gradient index rod lens provided with a refractive index gradient such that the refractive index decreases from the center of the lens outward. As a result, each of the end faces, i.e. the input face and the output face, of each of the lenses is a flat face perpendicular to the optical axis, and hence assembly such as joining the lenses together can be carried out easily. Moreover, because each of the lenses is cylindrical, the lenses can easily be housed in a cylindrical holder, and hence optical axis alignment is easy.

According to the fluorescence analysis optical multiplexer/demultiplexer of an embodiment, the first lens, the wavelength-selecting material portion, and the second lens are integrated together into a single body. As a result, the fluorescence analysis optical multiplexer/demultiplexer can be made to have a bonded together structure, and hence can be made compact.

As described in detail above, according to a fluorescence analysis optical module of the present invention, the fluorescence analysis optical module is comprised of an exciting light source that outputs exciting light of dominant wavelength $\lambda_1$, a fluorescence analysis optical multiplexer/demultiplexer that carries out multiplexing/demultiplexing on fluorescence of dominant wavelength $\lambda_2$, wherein $\lambda_2 > \lambda_1$, emitted from a sample onto which the exciting light has been irradiated via a probe or an optical connector, a detector that receives the fluorescence transmitted through the fluorescence analysis optical multiplexer/demultiplexer, a first optical transmission line that connects the fluorescence analysis optical multiplexer/demultiplexer to the exciting light source, a second optical transmission line that connects the fluorescence analysis optical multiplexer/demultiplexer to the probe or the optical connector, and a third optical transmission line that connects the fluorescence analysis optical multiplexer/demultiplexer to the detector. As a result, the exciting light can be led to the sample by the second optical transmission line, and the fluorescence from the sample can be led to the optical multiplexer/demultiplexer also by the second optical transmission line. The fluorescence analysis optical module can thus be made compact overall.

According to the fluorescence analysis optical module of an embodiment, the fluorescence analysis optical multiplexer/demultiplexer is comprised of a first lens that receives the exciting light and the fluorescence, and a wavelength-selecting material portion comprised of a dielectric multilayer film that receives the exciting light and the fluorescence transmitted through the first lens, wherein the optical axis of the first optical transmission line is offset from the center of the optical axis of the first lens such that the angle of incidence of the exciting light onto the wavelength-selecting material portion is substantially not more than 5°. As a result, compared with a conventional optical system in which the exciting light is made to be incident on the wavelength-selecting material portion at an angle of incidence of 45°, the angle of incidence of the exciting light can be made very low, and hence transmission leakage for the exciting light, which is comprised of a mixture of a P wave and an S wave, can be kept down.

According to the fluorescence analysis optical module of an embodiment, each of the first optical transmission line, the second optical transmission line, and the third optical transmission line is comprised of an optical fiber. As a result, the fluorescence analysis optical module can be made simple, and small in size.

According to the fluorescence analysis optical module of an embodiment, the fluorescence analysis optical module is constructed such that the probe has a fourth optical transmission line to which is connected another optical connector, and this other optical connector is connected to the above-mentioned optical connector. As a result, a simple optical system can be constructed.

According to the fluorescence analysis optical module of an embodiment, the exciting light source has an optical modulation mechanism. As a result, the detection sensitivity can be increased.

According to the fluorescence analysis optical module of an embodiment, the optical modulation mechanism is a lock-in modulation circuit that carries out lock-in in a range of 100 Hz to 10 KHz. As a result, the detection sensitivity can be increased reliably.

According to the fluorescence analysis optical module of an embodiment, the lock-in modulation circuit carries out optical modulation on the exciting light source with a rectangular wave. As a result, the measurement accuracy can be further increased.

According to the fluorescence analysis optical module of an embodiment, an optical isolator is provided between the exciting light source and the fluorescence analysis optical multiplexer/demultiplexer. As a result, returning exciting light can be prevented from entering the exciting light source.

According to the fluorescence analysis optical module of an embodiment, an edge filter that does not transmit light of the dominant wavelength $\lambda_1$ is provided between the fluorescence analysis optical multiplexer/demultiplexer and the detector. As a result, light outputted from the exciting light source can be reliably blocked from entering the detector.

As described in detail above, according to a fluorescence/photothermal conversion spectroscopic analyzer of the present invention, the fluorescence/photothermal conversion spectroscopic analyzer is comprised of a fluorescence analyzer as described above, a detecting light source that outputs detecting light of dominant wavelength $\lambda_3$, a photoelectric converter that detects a photothermal conversion signal intensity of the detecting light transmitted through a thermal lens produced in the sample by the exciting light, a photothermal conversion spectroscopic analysis optical multiplexer/demultiplexer that is comprised of a third lens, another wavelength-selecting material portion comprised of a dielectric multilayer film, and a fourth lens arranged in this order, and a fifth optical transmission line that connects the photothermal conversion spectroscopic analysis optical multiplexer/demultiplexer to the detecting light source, wherein the photothermal conversion spectroscopic analysis optical multiplexer/demultiplexer is disposed in the third optical transmission line, the photothermal conversion spectroscopic analysis optical multiplexer/demultiplexer receives the detecting light from the detecting light source via the third lens, and the fluorescence transmitted through the other wavelength-selecting material portion is received by the detector via the fourth lens. As a result, by irradiating the exciting light source used in the fluorescence measurement onto the sample, fluorescence analysis and photothermal conversion spectroscopic analysis can be carried out simultaneously.

According to the fluorescence/photothermal conversion spectroscopic analyzer of an embodiment, the dominant wavelength $\lambda_3$ satisfies the relationship $\lambda_1 < \lambda_2 < \lambda_3$. As a result, branching control of the detecting light by the optical multiplexer/demultiplexers can be carried out reliably.

According to the fluorescence/photothermal conversion spectroscopic analyzer of an embodiment, the detecting light source has an optical modulation mechanism. As a result, returning detecting light can be prevented from entering the detecting light source.

According to the fluorescence/photothermal conversion spectroscopic analyzer of an embodiment, the optical modulation mechanism is a lock-in modulation circuit that carries out lock-in in a range of 100 Hz to 10 KHz. As a result, the amount of light can be made stable even if there is optical or electrical noise.

As described in detail above, according to a fluorescence analysis chip of the present invention, the fluorescence analysis chip is comprised of plate-shaped element having a reflecting mirror in or close to a channel through which a sample is passed for detecting outputted light upon irradiating with exciting light via a lens, wherein the outputted light containing fluorescence reflected by the reflecting mirror and condensed by the lens is detected via the lens. As a result, LIF analysis can be carried out easily and with high sensitivity.

According to the fluorescence analysis chip of an embodiment, a surface of the channel onto which the exciting light is incident is flat, and another surface of the channel is curved. As a result, the reflecting mirror can be made to act as a condenser lens that condenses the fluorescence emitted from the sample in the channel, and hence LIF analysis can be carried out with higher sensitivity.

According to the fluorescence analysis chip of an embodiment, the reflecting mirror condenses the fluorescence to a position where the exciting light is condensed by the lens. As a result, the condensed fluorescence enters the lens reliably, whereby LIF analysis can be carried out with yet higher sensitivity.

According to the fluorescence analysis chip of an embodiment, the reflecting mirror is a metal film. As a result, the reflectance can be made to be high over a broad wavelength range in the visible region, and hence LIF analysis can be carried out with yet higher sensitivity.

According to the fluorescence analysis chip of an embodiment, the plate-shaped element are comprised of a first plate-shaped element having therein a groove constituting the channel, and a second plate-shaped element bonded to a groove-side surface of the first plate-shaped element, wherein the reflecting mirror is on a surface of the first plate-shaped element on the opposite side to the groove-side surface. As a result, the fluorescence emitted from the sample in the channel can be reliably detected via the lens through which the exciting light is irradiated, and hence LIF analysis can be carried out with higher sensitivity.

According to the fluorescence analysis chip of an embodiment, the plate-shaped element are comprised of a first plate-shaped element having therein a slit constituting the channel, and two second plate-shaped elements bonded respectively to the two surfaces of the first plate-shaped element, wherein the reflecting mirror is on surfaces of the slit, and between the first plate-shaped element and the one of the second plate-shaped elements that is bonded to the surface of the first plate-shaped element on the opposite side to the slit-side surface. As a result, the fluorescence emitted from the sample in the channel can be reliably detected via the lens through which the exciting light is irradiated, and hence LIF analysis can be carried out with higher sensitivity.

According to the fluorescence analysis chip of an embodiment, the plate-shaped element have therein segmenting channels for subjecting the sample to electrophoresis, and a separating channel that intersects with the segmenting channels, wherein the reflecting mirror is in a region of the separating channel from which the fluorescence emitted from the sample is led out. As a result, the resolution of an electrophoretic separation spectrum can be improved.

The invention claimed is:

1. A fluorescence analysis optical multiplexer/demultiplexer for use in a fluorescence analyzer that analyzes fluorescence of dominant wavelength $\lambda_2$ emitted from a sample onto which has been irradiated exciting light of dominant wavelength $\lambda_1$, wherein $\lambda_2 > \lambda_1$, the fluorescence analysis optical multiplexer/demultiplexer characterized by comprising:
   a first lens that receives the exciting light and the fluorescence;
   a wavelength-selecting material portion comprising a dielectric multilayer film that receives the exciting light and the fluorescence transmitted through said first lens; and
   a second lens that receives the fluorescence transmitted through said wavelength-selecting material portion.

2. A fluorescence analysis optical multiplexer/demultiplexer as claimed in claim 1, characterized in that said dielectric multilayer film is a long pass filter having a cutoff wavelength between the dominant wavelength $\lambda_1$ and the dominant wavelength $\lambda_2$.

3. A fluorescence analysis optical multiplexer/demultiplexer as claimed in claim 1, characterized in that a transmittance of said wavelength-selecting material portion to light of the dominant wavelength $\lambda_1$ is not more than −30 dB.

4. A fluorescence analysis optical multiplexer/demultiplexer as claimed in claim 1, characterized in that a transmittance of said wavelength-selecting material portion to light of the dominant wavelength $\lambda_2$ emitted from the sample is not less than −3 dB.

5. A fluorescence analysis optical multiplexer/demultiplexer as claimed in claim 1, characterized in that each of said first lens and said second lens is a cylindrical gradient index rod lens provided with a refractive index gradient such that a refractive index decreases from a center of the lens outward.

6. A fluorescence analysis optical multiplexer/demultiplexer as claimed in claim 1, characterized in that said first lens, said wavelength-selecting material portion, and said second lens are integrated together into a single body.

7. A fluorescence analysis optical module characterized by comprising:
   an exciting light source that outputs exciting light of dominant wavelength $\lambda_1$;
   a fluorescence analysis optical multiplexer/demultiplexer that carries out multiplexing/demultiplexing on fluorescence of dominant wavelength $\lambda_2$, wherein $\lambda_2 > \lambda_1$, emitted from a sample onto which the exciting light has been irradiated via a probe or an optical connector;
   a detector that receives the fluorescence transmitted through said fluorescence analysis optical multiplexer/demultiplexer;
   a first optical transmission line that connects said fluorescence analysis optical multiplexer/demultiplexer to said exciting light source;
   a second optical transmission line that connects said fluorescence analysis optical multiplexer/demultiplexer to said probe or said optical connector; and
   a third optical transmission line that connects said fluorescence analysis optical multiplexer/demultiplexer to said detector.

8. A fluorescence analysis optical module as claimed in claim 7, characterized in that said fluorescence analysis optical multiplexer/demultiplexer comprises a first lens that receives the exciting light and the fluorescence, and a wavelength-selecting material portion comprising a dielectric multilayer film that receives the exciting light and the fluorescence transmitted through said first lens, wherein an optical axis of said first optical transmission line is offset from a center of an optical axis of said first lens such that an angle of incidence of the exciting light onto said wavelength-selecting material portion is substantially not more than 5°.

9. A fluorescence analysis optical module as claimed in claim 7, characterized in that each of said first optical transmission line, said second optical transmission line, and said third optical transmission line comprises an optical fiber.

10. A fluorescence analysis optical module as claimed in claim 9, characterized in that each of said optical fibers is a single mode fiber.

11. A fluorescence analysis optical module as claimed in claim 7, characterized by being constructed such that said probe has a fourth optical transmission line to which is connected another optical connector, and said other optical connector is connected to said optical connector.

12. A fluorescence analysis optical module as claimed in claim 7, characterized in that said exciting light source has an optical modulation mechanism.

13. A fluorescence analysis optical module as claimed in claim 12, characterized in that said optical modulation mechanism is a lock-in modulation circuit that carries out lock-in in a range of 100 Hz to 10 KHz.

14. A fluorescence analysis optical module as claimed in claim 13, characterized in that said lock-in modulation circuit carries out optical modulation on said exciting light source with a rectangular wave.

15. A fluorescence analysis optical module as claimed in claim 7, characterized in that an optical isolator is provided between said exciting light source and said fluorescence analysis optical multiplexer/demultiplexer.

16. A fluorescence analysis optical module as claimed in claim 15, characterized in that an edge filter that does not transmit light of the dominant wavelength $\lambda_1$ is provided between said fluorescence analysis optical multiplexer/demultiplexer and said detector.

17. A fluorescence analyzer characterized by comprising:
a fluorescence analysis optical module as claimed in claim 7;
a sample stage on which are mounted plate-shaped element having therein a channel through which the sample is passed; and
a moving mechanism that carries out positioning by relatively moving at least one of said sample stage and said fluorescence analysis optical module.

18. A fluorescence/photothermal conversion spectroscopic analyzer characterized by comprising:
a fluorescence analyzer as claimed in claim 17;
a detecting light source that outputs detecting light of dominant wavelength $\lambda_3$;
a photoelectric converter that detects a photothermal conversion signal intensity of the detecting light transmitted through a thermal lens produced in the sample by the exciting light;
a photothermal conversion spectroscopic analysis optical multiplexer/demultiplexer that comprises a third lens, another wavelength-selecting material portion comprising a dielectric multilayer film, and a fourth lens arranged in this order; and
a fifth optical transmission line that connects said photothermal conversion spectroscopic analysis optical multiplexer/demultiplexer to said detecting light source;
wherein said photothermal conversion spectroscopic analysis optical multiplexer/demultiplexer is disposed at the midpoint of said third optical transmission line; said photothermal conversion spectroscopic analysis optical multiplexer/demultiplexer receives the detecting light from said detecting light source via said third lens; and the fluorescence transmitted through said other wavelength-selecting material portion is received by said detector via said fourth lens.

19. A fluorescence/photothermal conversion spectroscopic analyzer as claimed in claim 18, characterized in that the dominant wavelength $\lambda_3$ satisfies a relationship $\lambda_1 < \lambda_2 < \lambda_3$.

20. A fluorescence/photothermal conversion spectroscopic analyzer as claimed in claim 19, characterized in that a difference between the dominant wavelength $\lambda_3$ and the dominant wavelength $\lambda_2$ is in a range of 50 to 500 nm, and a chromatic aberration in the thermal lens between the dominant wavelength $\lambda_1$ and the dominant wavelength $\lambda_3$ is in a range of 20 to 200 nm.

21. A fluorescence/photothermal conversion spectroscopic analyzer as claimed in claim 18, characterized in that said detecting light source has an optical modulation mechanism.

22. A fluorescence/photothermal conversion spectroscopic analyzer as claimed in claim 21, characterized in that said optical modulation mechanism is a lock-in modulation circuit that carries out lock-in in a range of 100 Hz to 10 KHz.

23. A fluorescence analysis chip comprising plate-shaped element having therein a channel through which a sample is passed, the fluorescence analysis chip being disposed in a microchemical system having an irradiating device for irradiating exciting light having a predetermined wavelength onto the sample in said channel via a lens, and a detecting device for detecting outputted light from the sample in said channel, the fluorescence analysis chip characterized by having a reflecting mirror in or close to said channel, wherein said detecting device detects, via said lens, the outputted light containing fluorescence reflected by said reflecting mirror and condensed by said lens.

24. A fluorescence analysis chip as claimed in claim 23, characterized in that a surface of said channel onto which the exciting light is incident is flat, and another surface of said channel is curved.

25. A fluorescence analysis chip as claimed in claim 24, characterized in that said reflecting mirror condenses the fluorescence to a position where the exciting light is condensed by said lens.

26. A fluorescence analysis chip as claimed in claim 23, characterized in that said reflecting mirror is a metal film.

27. A fluorescence analysis chip as claimed in claim 23, characterized in that said plate-shaped element comprise a first plate-shaped element having therein a groove constituting said channel, and a second plate-shaped element bonded to a groove-side surface of said first plate-shaped element, wherein said reflecting mirror is on a surface of said first plate-shaped element on an opposite side to said groove-side surface.

28. A fluorescence analysis chip as claimed in claim 23, characterized in that said plate-shaped element comprise a first plate-shaped element having therein a slit constituting said channel, and two second plate-shaped elements bonded respectively to two surfaces of said first plate-shaped element, wherein said reflecting mirror is on surfaces of said slit, and between said first plate-shaped element and one of said second plate-shaped elements that is bonded to a surface of said first plate-shaped element on an opposite side to a slit-side surface.

29. A fluorescence analysis chip as claimed in claim 23, characterized in that said plate-shaped element have therein segmenting channels for subjecting the sample to electrophoresis, and a separating channel that intersects with said segmenting channels, wherein said reflecting mirror is in a region of said separating channel from which the fluorescence emitted from the sample is led out.

* * * * *